United States Patent [19]
Riley et al.

[11] 4,024,238
[45] May 17, 1977

[54] ORAL HYGIENE METHOD

[75] Inventors: William H. Riley, Midland; Herman J. Hendricks, Freeland, both of Mich.

[73] Assignee: The Dow Chemical Company, Midland, Mich.

[22] Filed: May 17, 1976

[21] Appl. No.: 686,754

[52] U.S. Cl. .................................................. 424/51
[51] Int. Cl.² .......................................... A61K 7/16
[58] Field of Search ............................... 424/48–58

[56] References Cited

UNITED STATES PATENTS 3,763,187  10/1973  Moyle .............................. 260/332.3

*Primary Examiner*—Shep K. Rose
*Attorney, Agent, or Firm*—Theodore Post; C. Kenneth Bjork

[57] ABSTRACT

4-Chlorophenyl-2-thenyliodonium chloride and similar salts are useful in the prevention of dental plaque and calculus, thereby minimizing or preventing gingivitis, caries and related periodontal disease.

3 Claims, No Drawings

ORAL HYGIENE METHOD

BACKGROUND OF THE INVENTION

The exact etiology of dental caries is not known with precision. Probably it results from a multiplicity of factors. It is well established, however, that caries is intimately involved with dental plaque and calculus, and that fluorides play an active role in the prevention of caries, rendering tooth enamel less susceptible to solubilization by the low pH of the plaque milieu.

Currently, fluorides are employed for tooth care as soluble inorganic fluorides to be taken internally such as in drinking water; as relatively insoluble fluoride salts, such as stannous fluoride in toothpaste formulations; or as applied directly to the teeth by a dentist. In recent years, it was found that certain organic amine hydrofluoride acid addition salts are effective in the prevention of dental caries, like the inorganic fluorides. The fluorides, however, as currently used have little or no effect on the formation of dental plaque.

Historically, the diphenyliodonium salts and substituted diphenyliodonium salts have been used as germicides and antiseptics. More recently, the thienyliodonium salts such as, for example, 4-chlorophenyl-2-thienyliodonium chloride, have been found to be much more effective as antimicrobials, since they have a broader spectrum of antimicrobial activity against both gram-positive and gram-negative and are more effective against microbes at lower concentrations; see, for example, U.S. Pat. No. 3,763,187, patented Oct. 2, 1973.

In research evaluating the application of antimicrobials for the control of specific microorganisms in the oral cavity implicated in the etiology of dental caries and periodontal disease, the unexpected discovery was made by us that antimicrobial activity can be separated from antiplaque activity. The dental literature has established and accepted the concept that plaque formation is a common factor in both dental caries and periodontal disease. It is taught in the dental literature that the organisms responsible for plaque formation reside primarily on tooth surfaces. The mechanism for their adherence to the tooth surface depends upon the synthesis of complex polysaccharides which, when synthesized in sufficient amounts, form the basis for plaque. Our unexpected observation is that certain thienyliodonium salts which also have antimicrobial activity at high concentrations and long exposure times have the ability at low concentrations and short exposure times to inhibit the formation of plaque without killing the organisms which cause plaque to be formed. Our research teaches that the ultimate removal of the specific organisms involved in plaque formation comes about not through the antimicrobial activity of the said compounds but through the prevention of plaque formation and the subsequent removal of the specific organisms by the abrasion due to the eating and ordinary oral hygiene such as brushing. Effective prevention of plaque formation requires consistent periodic utilization of the thienyliodonium salt, advantageously after meals, for a sufficient period of time. The following information supports this:

1. The basic activity of interest is the ability of the thienyliodonium salt to inhibit the formation of dental plaque but not to interfere with the viability of the organisms in question when treated with the level of the said salt for a short time period in the order of minutes. Studies show that time is a critical factor when considering this activity. Short contact periods apparently do not adversely affect the growth of *Streptococcus mutans*, the most important organism involved in plaque formation, but we know from our studies that intermittent daily usage in vivo is sufficient to inhibit the formation of plaque.

2. The mechanism by which plaque formation is inhibited has not been elucidated at this time. Sucrose from the environment of the plaque-forming organisms is converted through a series of metabolic and enzymatic steps into extracellular polysaccharides. These polysaccharides are the backbone of the plaque matrix. Inhibition, therefore, could occur at any point along this path.

3. The use of the thienyliodonium salts should not be presumed to take any particular form. Rather, any formulation that maintains the stability and activity characteristics of these salts is useful.

Both chlorhexidine and cetylpyridinium chloride (the latter available commercially as Micrin Plus mouthwash) have been used as anti-plaque agents; J. Periodont. Res. 8, 57–62, (1973) and J. Periodont. 40, 299, (1969).

SUMMARY OF THE INVENTION

This invention concerns contacting the oral cavity of a mammal with a small amount of a 4-chlorophenyl-2-thienyliodonium salt (i.e., the chloride, bromide, iodide, $C_{2-4}$ alkanoate, nitrate and trifluoroacetate, hereinafter referred to as Compound) for a short time period insufficient to inhibit the growth of oral flora whereby the formation of dental plaque is minimized or prevented, and, thereby calculus, gingivitis, caries and related periodontal disease are avoided. In the method of the invention, mouthwashes, toothpastes, tooth powders and concentrates are used which are buffered to give a pH between about 3 and about 7. The amount of Compound used ranges between about 1.0 and about 0.3 percent by weight of composition. The time of contact of the said preparation with the oral cavity ranges between about 30 seconds and about 5 minutes.

Description of Some Preferred Embodiments

The following additional description and examples further describe the invention and the manner and process of making and using it to enable the art-skilled to make and use the same and set forth the best mode contemplated by the inventors of carrying out the invention.

| Example 1: Mouthwash | |
|---|---|
| Compound, as chloride | 0.3% w/v |
| Alcohol U.S.P. | 10.0% v/v |
| Citrate Buffer, proportions of 9.5 ml 0.1 molar citric acid and 41.5 ml 0.1 molar sodium citrate diluted to 100 ml with distilled water to pH 6 q.s. | 100.0% v/v |

Other salt forms of Compound, as indicated above, are equally advantageous.

| Example 2: Mouthwash | | |
|---|---|---|
| Compound, as chloride | 0.3% | w/v |
| Alcohol U.S.P. | 15.0% | v/v |
| Sorbital Sol. U.S.P. | 10.0% | v/v |
| Glycerin | 5.0% | v/v |

-continued

| | |
|---|---|
| Sodium Saccharine | 0.15% w/v |
| Citric Acid Buffer to pH 5.75, q.s. | 100.0% v/v |
| Example 3: Mouthwash | |
| Compound, as chloride | 0.1% w/v |
| Alcohol U.S.P. | 15.0% v/v |
| Sorbital Sol. U.S.P. | 10.0% v/v |
| Glycerin | 5.0% v/v |
| Sodium Saccharine | 0.15% w/v |
| Citric Acid Buffer to pH 5.75 q.s. | 100.0% v/v |

EXAMPLE 4

Mouthwash

The formulation of Example 2 was modified to provide 0.1, 0.2 and 0.3% Compound wherein the pH was variously adjusted to 3.0 and 5.6. Otherwise, the formulations were exactly similar to that of Example 2.

In evaluating the plaque-inhibiting method of this invention, the following tests were used.

EXAMPLE 5

Wire Test for Plaque Inhibition

In this test, the procedure of McCabe et al., Arch. Oral Biol., 12 1653–1656 (December, 1967) was used. It was found that the plaque inhibition concentration of Compound as chloride was less than 2 parts per million (hereinafter p.p.m.).

EXAMPLE 6

Plaque Inhibition in a Hamster Model

A strain of *Streptococcus mutans* ATCC 10449, which is resistant to 500 µg/ml of streptomycin sulfate, was used. The inoculum was a 24 hour grown static in Todd-Hewitt broth with 0.5 percent lactalbumin hydrolysate added. All incubations were carried out under anaerobic conditions at 37° C under an atmosphere of 95 percent nitrogen + 5 percent carbon dioxide.

Engle Golden Syrian weanling hamsters were randomly distributed into cages of three animals of the same sex per cage. Experimental groups consisted of twelve animals, six males and six females. The hamsters were given food and deionized water ad libitum.

Diet 2000, obtained from General Biochemicals, and containing non-fat powdered milk, leaf meal alfalfa, whole wheat flour, powdered sucrose, iodized salt, desiccated liver and brewer's yeast, a highly cariogenic diet, was the only food supplied to the animals during the test. The ground diet was presented to the hamsters in stainless steel feeders designed to minimize waste. Consumption of the diet was monitored by weighing the feeders when they were refilled. This was done twice a week.

Formulations of Compound as chloride containing 0.1 percent, 0.2 percent and 0.3 percent Compound, individually buffered to pH 3.0 and 5.6, were used in this test. The basic mouthwash formulation is given in following Table 1 and the various combinations of Compound at the two pH's are given in following Table 2. The controls employed were as follows: Chlorhexidine gluconate (Atlas Chemical Co., G-4501) at a concentration of 0.3 percent w/v in distilled water, and Micrin Plus mouthwash (Johnson and Johnson, Lot 136222), which contains 0.025 percent cetylpyridinium chloride. The placebo was the basic mouthwash formulation. The order in which the groups were treated was determined by the use of random numbers.

TABLE 1

| Basic Mouthwash Formulation | |
|---|---|
| Ethyl Alcohol | 15.0% v/v |
| Sorbitol Solution | 10.0% v/v |
| Glycerine | 5.0% v/v |
| Buffer, q.s. to | 100.0% v/v |

TABLE 2

| Identification of Formulations | |
|---|---|
| Concentration of Compound* | pH |
| 0.1% | 5.6 |
| 0.2% | 5.6 |
| 0.3% | 5.6 |
| Placebo | 5.4 |
| 0.1% | 3.0 |
| 0.2% | 3.0 |
| 0.3% | 3.0 |
| Placebo | 3.0 |

*in basic mouthwash formulation

Twenty-four hours after arrival, the following inoculation regimen of the animals began. 100µl of *S. mutans* was injected into the mouth by means of an Eppendorf pipette, and 2 mils/100 mls. was added to the drinking water. This was repeated daily for four days. On the fifth day, fresh water was given to the hamsters. To insure that the organism actually was implanted in the oral cavity, swabs were taken on the sixth day. These cotton swabs were incubated in Todd-Hewitt broth supplemented with 0.5 percent lactalbumin hydrolysate and 500 µg/ml streptomycin sulphate for 48 hours. Plates of Mitis Salivarius agar (Difro) with 0.001 percent potassium tellurite were streaked from the swabs and checked for the purpose of *S. mutans*. It was present.

After swabbing, the treatment was begun. Appropriate formulations (Table 2) were administered by means of an Eppendorf pipette, 40 µl being placed on each row of molars located in the four quadrants of the mouth. This operation, repeated twice daily, gave a total of 160 µl per dose or 320 µl per day. After twenty-eight consecutive days of twice-daily treatment, the hamsters were sacrificed by the guillotine. The head was then skinned and stained for five seconds in a 1.0 percent aqueous solution of Erythrosin-B followed by a running water rinse. The teeth were then examined.

The evaluation of plaque present at the end of such a test is rather difficult to quantitate. Because of the obvious subjectivity of the method employed, the animals were processed randomly and presented to the scorer with only a code number. This blind technique attempted to reduce the opportunity for bias and increase the reliability of the readings obtained. In this fashion then, the hamster molars were examined under a stereo dissecting scope for the presence of plaque. Scores were given on the basis of an estimation of the percent of the tooth surface covered by the plaque. When the scoring was completed, representative specimens were photographed after an average three hour delay under 3X magnification on Ektachrome X to provide a permanent record of the results.

The data is percent of surface covered with plaque for each molar on both the maxillary and mandibular arch of each hamster are given in following Table 3.

TABLE 3

Percent of Molar Surface Covered With Plaque

| Treatment | Animal No. | Sex | Maxillaries Left 1 | 2 | 3 | Maxillaries Right 1 | 2 | 3 | Mandibles Left 1 | 2 | 3 | Mandibles Right 1 | 2 | 3 |
|---|---|---|---|---|---|---|---|---|---|---|---|---|---|---|
| Control | 72 | M | 15 | 10 | 15 | 20 | 10 | 15 | 20 | 15 | 10 | 20 | 5 | 5 |
| Uninoculated | 3 | M | 20 | 20 | 15 | 15 | 15 | 20 | 20 | 25 | 25 | 20 | 10 | 15 |
| | 81 | M | 10 | 10 | 15 | 10 | 15 | 15 | 10 | 5 | 5 | 15 | 10 | 5 |
| | 92 | M | 1 | 1 | 10 | 15 | 15 | 20 | 20 | 5 | 10 | 15 | 15 | 5 |
| | 25 | F | 25 | 20 | 30 | 30 | 30 | 40 | 15 | 10 | 10 | 20 | 10 | 5 |
| | 26 | F | 1 | 1 | 5 | 1 | 1 | 1 | 10 | 5 | 5 | 10 | 1 | 1 |
| Compound | 53 | M | 15 | 20 | 15 | 15 | 15 | 15 | 20 | 10 | 5 | 20 | 5 | 10 |
| 0.1%, pH 5.6 | 48 | M | 15 | 15 | 15 | 10 | 10 | 10 | 20 | 15 | 15 | 15 | 10 | 15 |
| | 67 | F | 20 | 15 | 25 | 10 | 15 | 20 | 20 | 10 | 10 | 20 | 15 | 15 |
| | 49 | F | 15 | 20 | 20 | 20 | 20 | 15 | 20 | 15 | 15 | 20 | 10 | 15 |
| | 66 | F | 5 | 5 | 5 | 1 | 10 | 10 | 5 | 5 | 5 | 1 | 5 | 15 |
| | 65 | M | 15 | 15 | 20 | 15 | 20 | 15 | 15 | 15 | 15 | 20 | 15 | 25 |
| | 50 | M | 10 | 10 | 15 | 15 | 15 | 15 | 15 | 15 | 15 | 20 | 10 | 15 |
| | 61 | M | 10 | 10 | 10 | 15 | 10 | 15 | 15 | 5 | 15 | 10 | 10 | 1 |
| | 51 | F | 15 | 20 | 15 | 15 | 15 | 20 | 50 | 15 | 10 | 20 | 15 | 10 |
| | 60 | F | 15 | 15 | 20 | 10 | 5 | 10 | 15 | 5 | 1 | 10 | 5 | 5 |
| Compound | 23 | M | 1 | 5 | 5 | 1 | 5 | 5 | 10 | 1 | 1 | 10 | 0 | 1 |
| 0.2%, pH 5.6 | 22 | M | 1 | 5 | 5 | 5 | 5 | 5 | 5 | 1 | 10 | 5 | 1 | 1 |
| | 6 | M | 1 | 1 | 5 | 1 | 5 | 5 | 0 | 1 | 1 | 5 | 5 | 1 |
| | 24 | F | 1 | 5 | 5 | 1 | 1 | 1 | 5 | 1 | 1 | 5 | 1 | 0 |
| | 93 | M | 15 | 5 | 5 | 15 | 15 | 15 | 30 | 20 | 20 | 40 | 20 | 15 |
| | 89 | M | 5 | 1 | 15 | 1 | 10 | 20 | 5 | 5 | 15 | 1 | 10 | 5 |
| | 74 | M | 20 | 5 | 15 | 30 | 20 | 30 | 20 | 10 | 5 | 30 | 15 | 20 |
| | 88 | F | 15 | 15 | 20 | 15 | 20 | 15 | 20 | 5 | 5 | 20 | 5 | 5 |
| | 13 | F | 15 | 20 | 20 | 15 | 25 | 20 | 30 | 10 | 15 | 10 | 5 | 10 |
| | 75 | F | 10 | 15 | 25 | 20 | 30 | 20 | 15 | 5 | 5 | 30 | 20 | 15 |
| Compound | 90 | M | 10 | 15 | 10 | 10 | 15 | 15 | 15 | 10 | 10 | 10 | 15 | 20 |
| 0.3%, pH 5.6 | 95 | M | 20 | 5 | 1 | 5 | 10 | 5 | 20 | 1 | 1 | 20 | 15 | 1 |
| | 19 | F | 1 | 1 | 1 | 5 | 5 | 1 | 5 | 1 | 1 | 5 | 1 | 5 |
| | 15 | F | 1 | 5 | 10 | 5 | 10 | 20 | 5 | 5 | 1 | 15 | 10 | 1 |
| | 21 | M | 0 | 1 | 5 | 1 | 5 | 1 | 5 | 1 | 1 | 1 | 0 | 1 |
| | 20 | M | 5 | 5 | 5 | 5 | 10 | 20 | 15 | 10 | 15 | 30 | 10 | 10 |
| | 91 | F | 5 | 20 | 20 | 15 | 15 | 20 | 20 | 15 | 10 | 10 | 10 | 15 |
| | 83 | F | 15 | 15 | 20 | 15 | 15 | 20 | 5 | 15 | 5 | 1 | 10 | 15 |
| | 94 | F | 20 | 15 | 1 | 20 | 10 | 5 | 30 | 10 | 15 | 25 | 10 | 5 |
| Placebo, | 96 | M | 15 | 15 | 20 | 15 | 15 | 40 | 20 | 20 | 25 | 30 | 20 | 30 |
| pH 5.6 | 80 | M | 20 | 20 | 30 | 30 | 20 | 30 | 20 | 15 | 20 | 40 | 20 | 25 |
| | 16 | F | 15 | 20 | 40 | 30 | 30 | 30 | 30 | 20 | 20 | 30 | 20 | 15 |
| | 18 | F | 30 | 30 | 40 | 20 | 30 | 50 | 20 | 10 | 10 | 20 | 20 | 20 |
| | 1 | M | 1 | 0 | 5 | 10 | 1 | 15 | 20 | 5 | 10 | 15 | 10 | 20 |
| | 27 | F | 5 | 1 | 5 | 1 | 5 | 5 | 10 | 5 | 5 | 15 | 5 | 1 |
| Compound | 7 | M | 1 | 5 | 5 | 5 | 1 | 5 | 1 | 1 | 5 | 1 | 0 | 1 |
| 0.1%, pH 3 | 76 | M | 15 | 10 | 20 | 20 | 20 | 15 | 30 | 15 | 10 | 20 | 10 | 5 |
| | 85 | M | 20 | 20 | 15 | 10 | 20 | 20 | 30 | 15 | 15 | 25 | 15 | 15 |
| | 33 | F | 15 | 15 | 20 | 15 | 15 | 10 | 10 | 5 | 5 | 20 | 5 | 10 |
| | 77 | F | 20 | 20 | 20 | 30 | 20 | 30 | 20 | 15 | 10 | 30 | 15 | 10 |
| | 86 | M | 1 | 5 | 1 | 10 | 10 | 5 | 10 | 5 | 5 | 15 | 5 | 5 |
| | 87 | M | 30 | 20 | 25 | 30 | 20 | 15 | 30 | 20 | 20 | 40 | 15 | 20 |
| | 78 | M | 15 | 15 | 15 | 10 | 15 | 20 | 30 | 20 | 15 | 40 | 10 | 15 |
| | 79 | F | 20 | 20 | 30 | 20 | 20 | 15 | 20 | 15 | 10 | 20 | 10 | 10 |
| | 84 | F | 15 | 10 | 5 | 10 | 5 | 5 | 20 | 10 | 5 | 20 | 10 | 15 |
| Compound | 44 | M | 30 | 40 | 40 | 30 | 30 | 25 | 15 | 10 | 5 | 20 | 15 | 15 |
| 0.2%, pH 3 | 64 | M | 20 | 20 | 10 | 30 | 20 | 20 | 15 | 10 | 15 | 30 | 20 | 20 |
| | 62 | M | 20 | 20 | 15 | 15 | 15 | 20 | 30 | 10 | 15 | 25 | 10 | 5 |
| | 42 | F | 20 | 20 | 10 | 15 | 5 | 10 | 20 | 5 | 5 | 10 | 5 | 5 |
| | 45 | F | 15 | 10 | 15 | 10 | 20 | 20 | 15 | 1 | 5 | 15 | 5 | 10 |
| | 46 | M | 15 | 15 | 15 | 10 | 5 | 5 | 20 | 5 | 5 | 20 | 15 | 10 |
| | 52 | M | 1 | 5 | 15 | 5 | 5 | 15 | 15 | 5 | 10 | 15 | 5 | 5 |
| | 34 | F | 10 | 20 | 30 | 10 | 15 | 40 | 15 | 10 | 10 | 30 | 10 | 20 |
| Compound | 17 | M | 5 | 5 | 1 | 1 | 5 | 10 | 1 | 1 | 0 | 1 | 1 | 1 |
| 0.3%, pH 3 | 4 | M | 1 | 5 | 10 | 5 | 10 | 15 | 10 | 10 | 5 | 20 | 10 | 1 |
| | 98 | F | 20 | 20 | 15 | 15 | 15 | 20 | 20 | 10 | 5 | 20 | 10 | 5 |
| | 82 | F | 20 | 20 | 15 | 20 | 20 | 20 | 15 | 15 | 5 | 20 | 5 | 1 |
| | 99 | F | 5 | 5 | 10 | 5 | 10 | 5 | 5 | 1 | 5 | 10 | 10 | 1 |
| | 28 | M | 5 | 5 | 5 | 1 | 5 | 5 | 5 | 1 | 5 | 10 | 5 | 5 |
| | 29 | M | 1 | 1 | 5 | 0 | 1 | 1 | 5 | 1 | 0 | 1 | 0 | 0 |
| | 30 | M | 5 | 5 | 5 | 1 | 5 | 5 | 1 | 1 | 1 | 10 | 5 | 5 |
| | 73 | F | 20 | 15 | 15 | 15 | 10 | 15 | 30 | 10 | 10 | 25 | 15 | 15 |
| | 97 | F | 25 | 20 | 25 | 20 | 15 | 15 | 40 | 20 | 10 | 15 | 10 | 5 |
| | 100 | F | 20 | 15 | 20 | 15 | 15 | 10 | 20 | 20 | 5 | 20 | 10 | 5 |
| Placebo, | 9 | M | 30 | 30 | 40 | 30 | 30 | 30 | 25 | 20 | 25 | 40 | 30 | 25 |
| pH 3 | 8 | M | 30 | 30 | 25 | 30 | 30 | 40 | 30 | 10 | 10 | 50 | 10 | 15 |
| | 32 | F | 20 | 20 | 30 | 20 | 20 | 30 | 20 | 15 | 15 | 15 | 5 | 10 |
| | 31 | F | 30 | 25 | 25 | 20 | 20 | 15 | 40 | 30 | 30 | 30 | 20 | 20 |
| | 15 | M | 5 | 10 | 15 | 10 | 5 | 10 | 25 | 10 | 5 | 20 | 10 | 5 |
| | 14 | M | 25 | 25 | 30 | 25 | 15 | 10 | 15 | 5 | 1 | 20 | 5 | 10 |
| | 11 | F | 5 | 10 | 15 | 5 | 5 | 10 | 15 | 15 | 10 | 20 | 5 | 5 |
| | 12 | F | 30 | 30 | 40 | 30 | 30 | 30 | 40 | 30 | 25 | 35 | 25 | 25 |
| Control | 35 | M | 10 | 10 | 15 | 15 | 15 | 20 | 20 | 15 | 10 | 20 | 10 | 5 |
| Inoculated | 36 | M | 5 | 1 | 30 | 5 | 5 | 20 | 20 | 15 | 20 | 15 | 1 | 10 |
| | 70 | F | 30 | 20 | 50 | 20 | 10 | 5 | 60 | 15 | 30 | 30 | 15 | 15 |
| | 71 | F | 15 | 15 | 20 | 15 | 10 | 10 | 20 | 20 | 20 | 30 | 15 | 20 |
| | 58 | M | 20 | 20 | 15 | 10 | 15 | 15 | 30 | 15 | 5 | 25 | 10 | 15 |
| | 57 | M | 20 | 15 | 15 | 15 | 10 | 5 | 20 | 15 | 15 | 20 | 15 | 15 |
| | 56 | M | 15 | 10 | 15 | 15 | 10 | 15 | 20 | 10 | 10 | 20 | 15 | 10 |
| | 37 | F | 15 | 15 | 15 | 15 | 20 | 15 | 15 | 10 | 10 | 20 | 5 | 5 |
| Chlorhexidine, | 2 | M | 30 | 20 | 30 | 20 | 15 | 20 | 30 | 30 | 20 | 30 | 10 | 15 |
| 0.3% | 10 | F | 5 | 5 | 10 | 5 | 5 | 5 | 10 | 1 | 1 | 10 | 5 | 5 |
| | 63 | M | 5 | 1 | 5 | 5 | 5 | 1 | 10 | 1 | 1 | 5 | 1 | 5 |

TABLE 3-continued

| | | | Percent of Molar Surface Covered With Plaque | | | | | | | | | | |
|---|---|---|---|---|---|---|---|---|---|---|---|---|---|
| | | | Maxillaries | | | | | | Mandibles | | | | |
| | | | Left | | | Right | | | Left | | | Right | |
| Treatment | Animal No. | Sex | 1 | 2 | 3 | 1 | 2 | 3 | 1 | 2 | 3 | 1 | 2 | 3 |
| | 69 | M | 1 | 5 | 5 | 10 | 5 | 10 | 30 | 10 | 15 | 20 | 5 | 5 |
| | 43 | M | 5 | 10 | 10 | 10 | 5 | 5 | 20 | 10 | 5 | 25 | 10 | 15 |
| | 47 | F | 15 | 15 | 20 | 20 | 10 | 5 | 20 | 10 | 5 | 15 | 10 | 10 |
| | 68 | F | 10 | 5 | 25 | 5 | 10 | 30 | 20 | 5 | 10 | 20 | 10 | 10 |
| Micrin Plus | 54 | M | 15 | 20 | 15 | 10 | 10 | 15 | 30 | 10 | 10 | 20 | 15 | 15 |
| (CPC-0.025%) | 59 | M | 20 | 20 | 30 | 15 | 15 | 20 | 25 | 15 | 10 | 20 | 15 | 5 |
| | 40 | F | 30 | 25 | 30 | 20 | 20 | 30 | 25 | 15 | 20 | 30 | 20 | 20 |
| | 55 | F | 15 | 15 | 10 | 10 | 15 | 10 | 20 | 15 | 15 | 15 | 5 | 15 |
| | 41 | F | 20 | 30 | 15 | 30 | 30 | 20 | 30 | 10 | 10 | 40 | 10 | 5 |
| | 39 | F | 20 | 20 | 30 | 15 | 20 | 35 | 30 | 15 | 20 | 30 | 15 | 15 |
| | 38 | F | 5 | 5 | 15 | 5 | 5 | 10 | 15 | 5 | 5 | 20 | 5 | 10 |

Following Table 4 gives the amount of diet that was consumed during the course of the experiment in grams per cage. Due to the frailty of the hamster, some deaths occurred during the test. Because of this, the number of animals in certain cages was less than three. Therefore, the death factor was taken into account in drawing conclusions from the consumption data.

TABLE 4

| | Food Consumption | |
|---|---|---|
| Treatment | Sex | Diet 2000 Consumed (Grams/Cage) |
| Control, Uninoculated | M | 634 |
| | F | 297 |
| | M | 582 |
| | F | 538 |
| Compound, 0.1%, pH 5.6 | M | 556 |
| | F | 750 |
| | M | 738 |
| | F | 644 |
| Compound, 0.2%, pH 5.6 | M | 752 |
| | F | 298 |
| | M | 744 |
| | F | 828 |
| Compound, 0.3%, pH 5.6 | M | 517 |
| | F | 585 |
| | M | 519 |
| | F | 699 |
| Placebo, pH 5.6 | M | 557 |
| | F | 549 |
| | M | 399 |
| | F | 393 |
| Compound, 0.1%, pH 3.0 | M | 715 |
| | F | 612 |
| | M | 1333 |
| | F | 645 |
| Compound, 0.2%, pH 3.0 | M | 677 |
| | F | 612 |
| | M | 525 |
| | F | 543 |
| Compound, 0.3%, pH 3.0 | M | 598 |
| | F | 620 |
| | M | 642 |
| | F | 718 |
| Placebo, pH 3.0 | M | 664 |
| | F | 515 |
| | M | 577 |
| | F | 525 |
| Control, Inoculated | M | 595 |
| | F | 413 |
| | M | 677 |
| | F | 384 |
| Chlorhexidine, 0.3% | M | 355 |
| | F | 318 |
| | M | 666 |
| | F | 611 |
| Micrin Plus (CPC-0.025%) | M | 502 |
| | F | 644 |
| | F | 517 |

The first analysis of the data examined the effect of pH. Comparisons were made using the Student $t$ test, and significance was determined at $p = 0.05$ (Table 5). From these calculations, it was learned that pH did not significantly alter the results at any concentration. Because of this, the data generated for a given level of treatment was placed into one group, thus simplifying further manipulations.

TABLE 5

| Statistical Comparison of Compound Formulations at pH 3.0 and 5.6 | | | | | |
|---|---|---|---|---|---|
| Treatment | $\bar{x} \pm$ S.E. | $\Delta \bar{x}$ | $t$calculated | df | $t_{p=05}$ |
| 0.3%, pH 5.6 | 9.63±1.86 | | | | |
| 0.3%, pH 3.0 | 9.57±1.59 | 0.06 | 0.025 | 18 | 2.101 |
| 0.2%, pH 5.6 | 14.86±1.81 | | | | |
| 0.2%, pH 3.0 | 10.34±2.19 | 4.52 | 1.592 | 16 | 2.120 |
| 0.1%, pH 5.6 | 14.42±2.06 | | | | |
| 0.1%, pH 3.0 | 14.27±1.23 | 0.15 | 0.063 | 18 | 2.101 |
| Placebo, 5.4 | 20.79±2.90 | | | | |
| Placebo, 3.0 | 18.20±3.52 | 2.59 | 0.567 | 12 | 2.179 |

Considering the data as a whole, the arithmetic means ± the standard error for each treatment was calculated. These values were:

| Treatment | $\bar{x}\% \pm$ S.E. |
|---|---|
| Compound  − 0.1% | 14.3±1.2[a] |
|  − 0.2% | 12.4±1.5[b] |
|  − 0.3% | 9.6±1.2[c] |
| Chlorhexidine, 0.3% | 11.3±2.3[b] |
| Micrin Plus | 17.0±1.9 |
| Placebo | 19.7±2.2 |

Superscript = level of significance; no superscript = no significance
[a] = p <0.05; [b] = p <0.02; [c] = p <0.001

From the data obtained, it has been established that pH, in the range tested, does not influence the activity of the mouthwash formulations containing Compound. The use of the lower pH, however, may give rise to some question concerning its effect on the mouth. It is noted that materials with a pH in the vicinity of 3 are frequently introduced into the mouth. Two good examples are carbonated beverages and presently available mouthwash formulations. Many soft drinks have a pH in the range of 2.5 to 3.0 because of the dissolved $CO_2$ present. A check of some common mouthwashes gave the following results:

| Mouthwash | pH |
|---|---|
| Chloraseptic[R] (Eaton) | 8.7 |
| Lavoris[R] (Vick) | 2.9 |
| Listerine[R] (Warner-Lambert) | 4.3 |
| Micrin Plus (Johnson & Johnson) | 5.5 |
| Scope[R] (Procter & Gamble) | 5.5 |

This demonstrates that a wide range of pH is tolerated in the mouth. Additionally, when the hamsters were treated with the mouthwash, they did not react toward the low pH formulation, and upon gross examination of the tongue, palate, gingiva, and surrounding tissues, no edema, redness, or other irritation was noted. One can see from calculated values of $\bar{x}\%\pm$ S.E. (table following Table 5) that Compound at a concentration of 0.3 percent was most effective in inhibiting plaque in this test. Concentrations of 0.2 percent and 0.1 percent were also active, but the results were not so dramatic.

Another useful tool for determining the effectiveness of a treatment is the Plaque Score (PS). The PS for a given treatment is defined as the placebo value divided by the test value, or:

$$PS = \frac{\bar{x} \text{ of Molar Surface with Plaque in Placebo Group}}{\bar{x} \text{ of Molar Surface with Plaque in Test Group.}}$$

By definition, then, the placebo group has a PS of 1. Groups with a PS<1 are not effective in inhibiting plaque while those with a PS>1 exhibit some activity. Due to the variability encountered in biological experimentation, this ratio becomes extremely useful in the normalization of data and allows treatments from many experiments to be compared. The plaque scores from this experiment are as follows:

| Group | | Plaque Score (PS) |
|---|---|---|
| Compound | − 0.1% | 1.38 |
| | − 0.2% | 1.59 |
| | − 0.3% | 2.05 |
| Chlorhexidine, 0.3% | | 1.74 |
| Micrin Plus | | 1.16 |

A formulation containing 0.3 percent Compound, which has a PS = 2.05, is, then, a significant level of treatment, as supported also by prior statistics performed on test data.

From the test data as well as controls, it appeared that the animals were naturally infected with plaque-forming organisms before the test was begun. Even though this may be the case, the results of this experiment show that Compound is effective in treating not only artifically introduced infections but also naturally occurring ones.

EXAMPLE 7

Plaque Inhibition in a Rat Model

Test groups of six Osborne-Mendel rats per cage were fed the cariogenic Diet 2000 and deionized water ad libitum. The teeth of the test groups were rinsed twice daily for 7 to 28 days with one of the following rinses: water, aqueous 0.1 percent Compound (as chloride), aqueous 0.2 percent Compound (as chloride), aqueous 0.3 percent Compound (as chloride), aqueous formulation minus Compound and a blank wherein nothing was used. The data obtained were as follows:

TABLE 6

Plaque Accumulations in Rats Receiving Various Rinses Twice Daily for 7 to 28 Days

| Treatment | N | 7 Days $\bar{x}$ | N | 28 Days $\bar{x}$ |
|---|---|---|---|---|
| Water | 6 | 1.31 (0.36)* | 6 | 1.28 (0.56) |
| Compound 0.1% | 6 | 0.70 (0.51) | 6 | 0.70 (0.56) |
| Compound 0.2% | 6 | 0.38 (0.26) | 6 | 0.70 (0.27) |
| Compound 0.3% | 6 | 0.40 (0.30) | 6 | 0.42 (0.18) |

TABLE 6-continued

Plaque Accumulations in Rats Receiving Various Rinses Twice Daily for 7 to 28 Days

| Treatment | N | 7 Days $\bar{x}$ | N | 28 Days $\bar{x}$ |
|---|---|---|---|---|
| Chlorhexidine 0.72% | 6 | 0.56 (0.31) | 6 | 0.31 (0.25) |
| Formulation minus Compound | 6 | 0.90 (0.19) | 6 | 1.20 (0.34) |
| None | 4 | 0.90 (0.44) | 6 | 1.22 (0.25) |
| | | $F_{6,33}=5.9$ | | $F_{6,33}=5.0$ |
| | | $P<.0005$ | | $p<.002$ |

*( ) = standard deviation

EXAMPLE 8

Kill Time Tests on Compound

Organism: *Streptococcus mutans*, ATCC 10449-SR 500µg*

Procedure:

The reaction flask (sterile distilled water ± 0.3% w/v Compound, as chloride) was inoculated with the desired concentration of *S. mutans* 24 hours old culture grown at 37° C under 95% $N_2$ + 5% $CO_2$ in Todd Hewitt broth + 0.5% lactalbumin hydrolysate. Samples were removed at intervals (contact times below) and diluted out for determination of viability. The appropriate dilution was filtered through a 0.45µ pore size membrane filter and the filter was washed with 100 mls of buffer to remove any remaining traces of test material. The filter was then placed on an agar plate containing the medium enumerated above and incubated as before.

Results: Viability of S. mutans (CFU/ml**)

| | Challenge and System Tested | | | |
|---|---|---|---|---|
| | $1.4 \times 10^6$ CFU/ml | | $1.4 \times 10^8$ CFU/ml | |
| Contact Time | Control | 0.3% Compound | Control | 0.3% Compound |
| 30 seconds | $1.6 \times 10^6$ | $1.5 \times 10^6$ | $1.7 \times 10^8$ | $1.5 \times 10^8$ |
| 1 minute | $1.5 \times 10^6$ | $1.5 \times 10^6$ | $1.6 \times 10^8$ | $1.6 \times 10^8$ |
| 5 minutes | $1.6 \times 10^6$ | $1.4 \times 10^6$ | $1.6 \times 10^8$ | $1.6 \times 10^8$ |

*This isolate of the type culture is resistant to 500 µg/ml of streptomycin sulfate
**Colony Forming Units Analysis:

Statistical analysis of the results showed that there were no significant differences between groups (p = 0.25 and less), i.e., at contact times of 30 seconds to 5 minutes, Compound as chloride at 0.3% w/v had no significant effect on the viability of *S. mutans*.

What is claimed is:

1. A method for inhibiting plaque formation in the mouth of a mammal which comprises periodically contacting the oral cavity inclusive of the teeth with a concentration of between 0.1 and 0.3 weight percent of a 4-chlorophenyl-2-thienyliodonium salt in a pharmaceutically-acceptable vehicle for a time ranging between about thirty seconds and about five minutes.

2. The method of claim 1 wherein the pharmaceutically-acceptable vehicle is an aqueous vehicle buffered to a pH ranging between about 3 and about 6.

3. The method of claim 1 wherein the active ingredient and the pharmaceutically-acceptable vehicle, in combination, consist of the following ingredients in the following proportions: 4-chlorophenyl-2-thienyliodonium chloride 0.1–0.3% w/v, alcohol 15.0% v/v, sorbitol 10.0% v/v, glycerine 5.0% v/v, sodium saccharine 0.15% w/v and citric acid buffer q.s. 100% v/v to give a pH of about 6.

* * * * *

UNITED STATES PATENT AND TRADEMARK OFFICE
CERTIFICATE OF CORRECTION

PATENT NO. : 4,024,238
DATED : May 17, 1977
INVENTOR(S) : William H. Riley, Herman J. Hendricks It is certified that error appears in the above-identified patent and that said Letters Patent are hereby corrected as shown below:

Column 1, line 29, "gram-negative and" should read --gram-negative organisms and--.

Column 1, line 58, "due to the eating" should read --due to eating--.

Column 2, line 39, "1.0" should read --0.1--.

Column 3, line 37, "hour grown" should read --hour culture grown--.

Column 4, line 27, "mils/100" should read --mls./100--.

Column 4, line 37, "purpose" should read --presence--.

Column 4, line 66, "is" should read --in--.

Column 5, Table 3, line 10, Animal No. 25, should read

--F   25   20   50   30   30   40   15   10   10   20   10   5--.

Column 8, line 31, "means" should read --mean--.

Column 9, line 3, "x%" should read --$\bar{x}$%--.

Column 9, line 44, "artifically" should read --artificially

UNITED STATES PATENT AND TRADEMARK OFFICE
CERTIFICATE OF CORRECTION

PATENT NO. : 4,024,238

DATED : May 17, 1977

INVENTOR(S) : William H. Riley, Herman J. Hendricks

It is certified that error appears in the above-identified patent and that said Letters Patent are hereby corrected as shown below:

Column 10, line 22, "hours" should read --hour--.

Signed and Sealed this

First Day of November 1977

[SEAL]

Attest:

RUTH C. MASON
*Attesting Officer*

LUTRELLE F. PARKER
*Acting Commissioner of Patents and Trademarks*